United States Patent [19]

Ito et al.

[11] 4,357,938
[45] Nov. 9, 1982

[54] DISPOSABLE DIAPER

[75] Inventors: Osamu Ito, Utsunomiya; Harumasa Yamasaki, Wakayama; Kazunori Nishizawa, Funabashi, all of Japan

[73] Assignee: Kao Soap Co., Ltd., Tokyo, Japan

[21] Appl. No.: 278,296

[22] Filed: Jun. 26, 1981

[30] Foreign Application Priority Data

Aug. 7, 1980 [JP] Japan .............................. 55-108583

[51] Int. Cl.³ .............................................. A41B 13/02
[52] U.S. Cl. ................................................. 128/287
[58] Field of Search ............... 128/284, 286, 287, 288, 128/290 R, 290 W

[56] References Cited

U.S. PATENT DOCUMENTS

| | | | |
|---|---|---|---|
| 3,589,364 | 6/1971 | Dean et al. | 128/290 R |
| 3,731,686 | 5/1973 | Chatterjee | 128/290 R |
| 4,050,462 | 9/1977 | Woon et al. | 128/287 |
| 4,246,900 | 1/1981 | Schröder | 128/287 |

Primary Examiner—C. Fred Rosenbaum
Attorney, Agent, or Firm—Flynn, Thiel, Boutell & Tanis

[57] ABSTRACT

A disposable diaper comprising a water-absorbing layer located between a liquid-permeable surface sheet and a liquid-impermeable backing sheet, wherein water-absorbing shrinkable fibers, which shrink in the direction of the fiber length and are rendered elastic on absorption of water, are fixed to and extend along the central portion in the lengthwise direction of the disposable diaper in such a manner that the water-absorbing shrinkable fibers are not placed on top of the water-absorbing layer, and wherein means is provided so that the water-absorbing shrinkable fibers become wetted when the diaper is wetted, said water-absorbing shrinkable fibers exhibiting a percent shrinkage of at least 15% and a shrinking force of at least 100 g when said fibers are wetted.

10 Claims, 3 Drawing Figures

DISPOSABLE DIAPER

The present invention relates to a disposable diaper having a leakage-preventing structure. More particularly, the present invention relates to a disposable diaper in which the edge portions that contact the skin in the crotch portion of the wearer shrink and are rendered elastic when the diaper is wetted and absorbs liquid.

Various disposable diapers have heretofore been proposed. In most conventional disposable diapers, a low-density polyethylene film is used as a liquid-impermeable backing sheet, and a fluffed pulp wrapped stably with tissue paper is placed, as an absorbing layer, on the liquid-impermeable sheet. Furthermore, there has recently been proposed a disposable diaper in which there is employed, as an absorbent, a solid of a highly water-absorbing polymer capable of absorbing an amount of water several times the weight of the polymer, such as polyacrylic acid derivatives or carboxymethylated pulp fiber.

A non-woven fabric is conventionally used as a liquid-permeable porous sheet placed on top of the absorbing layer. Moreover, a polyethylene film having many fine through holes also is marketed as a liquid-permeable sheet.

Ordinarily, disposable diapers are fabricated by attaching an adhesive tape, for fixing the diaper to the body of the wearer, to a disposable diaper proper which comprises a liquid-permeable surface sheet, a liquid-impermeable back sheet and an absorbing layer interposed between the two sheets. As shown in Japanese Patent Publication No. 40267/77 and Japanese Patent Application Laid-Open Specifications No. 115939/79 and No. 120045/77, there have recently been proposed disposable diapers in which an elastic number is provided along the edge portion in the lengthwise direction of the diaper and gathering is formed on the edge portion in order to tightly fit the diaper to the crotch portion of the wearer. In diapers of this type, because the elastic shrinking force of an elastic member, such as rubber, is utilized, if the diaper is attached to the body for a long time, the covered portion of the body is closely sealed and traps odors. Furthermore, diapers of this type are defective in that a compressive feel is imparted to the wearer. On the other hand, these diapers are advantageous in that because of the presence of the elastic member, the diaper fits well to the body and discharged liquid scarcely leaks out.

Such disposable diapers including an elastic member involve disadvantages in connection with the manufacturing process and transportation, in addition to the above-mentioned defects. More specifically, in the production of these diapers, the elastic member is attached to the diaper proper in a state in which the elastic member is stretched or the edge portion of the diaper proper is contracted and wrinkled. This operation is very troublesome and the manufacturing efficiency is lowered. Furthermore, in the product diaper, since the elastic member is shrunk, the diaper is wrinkled as a whole and is bulky, and therefore the transportation cost is increased.

We previously filed a patent application covering water-absorbing fibers which shrink for the first time when they absorb water (Japanese Patent Application No. 83390/80). We conducted further research and discovered that when a structure formed of such water-absorbing fibers is arranged in the edge portion of a diaper in the lengthwise direction, in place of the conventional elastic member, the foregoing disadvantages of the conventional disposable diapers are eliminated. We have now completed the present invention based on this discovery.

More specifically, in accordance with the present invention, there is provided a disposable diaper comprising a liquid-permeable surface sheet, a liquid-impermeable back sheet, a water-absorbing layer located between the two sheets and water-absorbing shrinkable fibers, which shrink in the direction of the fiber length and are rendered elastic an absorption of water, are mounted on and extend along the central portion in the lengthwise direction of the disposable diaper in such a manner that the water-absorbing shrinkable fibers are not placed on top of the water-absorbing layer, and wherein means are provided for wetting the water-absorbing shrinkable fibers when the diaper is wetted and when said water-absorbing shrinkable fibers are wetted, the percent shrinkage of said water-absorbing shrinkable fibers is at least 15% and the shrinking force of said water-absorbing shrinkable fibers is at least 100 g.

The present invention will now be described in detail with reference to embodiments illustrated in the accompanying drawings.

Figure 1:
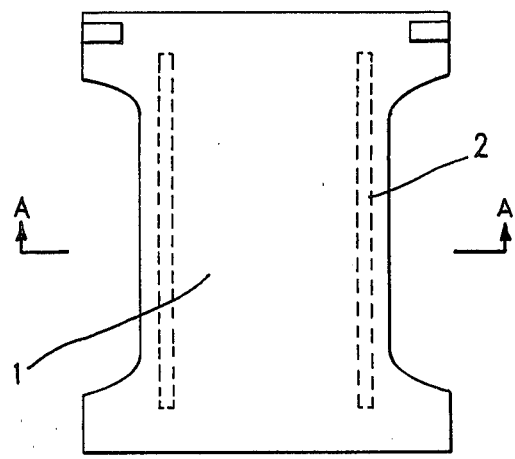
FIG. 1 is a plan view showing a disposable diaper according to the present invention, in the flat, as-manufactured, state.

In the drawings, the reference numerals identify the following elements: 1, disposable diaper; 2, water-absorbing shrinkable fibers; 3, liquid-permeable surface sheet; 4, water-absorbing layer; 5, water-absorbing paper; and 6, liquid-impermeable back sheet.

Figure 3:
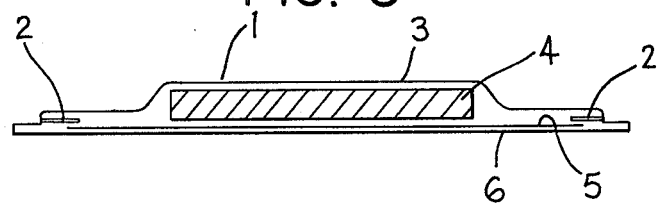
FIG. 3 is a sectional view taken along the line A—A in FIG. 1.

FIG. 1 is a plan view showing a disposable diaper, and FIG. 3 is a view showing a section taken along the line A—A in FIG. 1. As is apparent from FIG. 3, this disposable diaper comprises a water-absorbing layer 4 interposed between a liquid-permeable surface sheet 3 and a liquid-impermeable back sheet 6 and covered by both of the sheets. The known materials described hereinbefore are used for these structural elements in the present invention. The most characteristic feature of the present invention is that water-absorbing shrinkable fibers 2 are included in this diaper. The water-absorbing shrinkable fibers 2 are fixed to both of the side edges of the diaper and are located directly between the surface sheet 3 and back sheet 6. The water-absorbing shrinkable fibers extend along the central portion in the lengthwise direction of the diaper 1. The water-absorbing fibers 2 are not placed directly above or below the water-absorbing layer, but rather, are laterally spaced from the water-absorbing layer, as shown in FIGS. 1 and 3. Fixing of the water-absorbing shrinkable fibers can be accomplished by conventional methods, such as bonding same with an adhesive, sewing and/or heat bonding same by fusing same to the back sheet 6. In the present invention, it is important that the characteristic property of the water-absorbing shrinkable fibers 2, that is, the property of being shrunk lengthwise and rendered elastic on contact with water, should be imparted to the disposable diaper 1 including the layers 3 and 6. Accordingly, a method of fixing the water-absorbing shrinkable fibers 2 by using a large amount of a non-elastic medium, such as an adhesive, is not preferred. Furthermore, because the properties of the water-absorbing shrinkable fibers 2 are changed on contact with water, it is necessary to provide means for guiding some of the liquid to the water-absorbing shrinkable fibers 2 when the disposable diaper 1 is wetted. Ordinarily, even when the disposable diaper absorbs urine, urine which has not been absorbed in the water-absorbing layer 4 or urine which after it has once been absorbed in the water-absorbing layer 4, is squeezed out therefrom by the body weight of a baby, is transferred to the water-absorbing shrinkable fibers 2 by means of the surface sheet 3 or the back sheet 6, with the result being that the water-absorbing shrinkable fibers 2 become wet. Accordingly, special means for guiding liquid to the water-absorbing shrinkable fibers 2 need not be provided. However, in the embodiment shown in FIG. 3, in order to enhance this transfer effect, a water-absorbing paper 5 is placed on the back sheet 3 to act as a liquid-transmitting bridge between the water-absorbing layer 4 and the water-absorbing shrinkable fibers 2, so that water once absorbed in the layer 4 is promptly transferred to the water-absorbing shrinkable fibers 2. The water-absorbing paper 6 can be located not only on the back sheet 6, but also, below the surface sheet 3 or in the water-absorbing layer 4 which is formed to have a multi-layer structure, and in each case, the intended effect can be attained satisfactorily.

Figure 2:
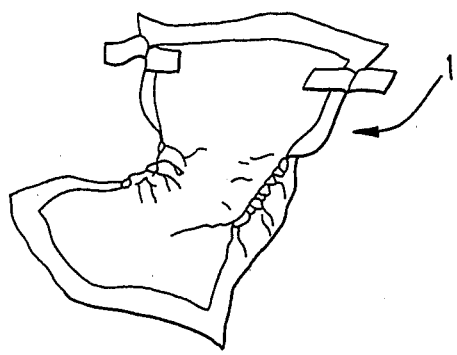
FIG. 2 is a perspective view diagrammatically illustrating the state of the diaper after the water-absorbing shrinkable fibers have absorbed liquid.

In the disposable diaper of the present invention having the above-mentioned structure, when the diaper absorbs liquid, the water absorbing shrinkable fibers 2 shrink, and therefore, also the length of the edge portions in the lengthwise direction becomes wrinkled, puckered and folded as shown in FIG. 2. Since the water-absorbing shrinkable fibers 2 are simultaneously rendered elastic, they closely seal the crotch portion of the wearer according to the shape thereof whereby to prevent leakage of fluid.

Since the water-absorbing fibers 2 are not shrunk or elastic before they are used and wetted, the diaper of the present invention can be handled at the production and transportation steps in the same manner as conventional diapers, and therefore, reduction of the manufacturing and transporting efficiencies does not occur. Furthermore, so long as the amount of absorbed fluid is still small, that is, while the water-absorbing layer 4 is still capable of absorbing more water therein, the elastic compression force applied on the skin of the wearer is moderated and the crotch portion or the like is prevented from getting musty. When the amount of the absorbed fluid is increased, a stronger seal against escape of liquid is formed between the crotch portion of the wearer and the diaper. The percent shrinkage and shrinking force of the water-absorbing shrinkable fibers 2 have important influences on preventing leakage of fluid. In order for the diaper to exhibit satisfactory functions, it is necessary that the percent shrinkage of the fibers 2 should be at least 15% and the elastic shrinking force should be at least 100 g. An optimum value of the precent shrinkage depends on the dimensions of the crotch portion of a wearer and the length of the water-absorbing fibers. Ordinarily, the length of the disposable diaper is about 5 to 10% oversize, and therefore, the percent shrinkage should be at least 15%. In order to produce a good liquid seal, the sides of the diaper should move appropriately and in close conformity with the movement of the legs of the wearer. For this purpose, the shrinking force should be at least 100 g. If the shrinking force is smaller than 100 g, the seal is broken and there is a risk of leakage of fluid.

In the present invention, the percent shrinkage means the degree of shrinkage of the side edges of the diaper of the present invention, including the water-absorbing shrinkable fibers, when the water-absorbing shrinkable fibers are wetted with urine. It is expressed by the formula:

percent shrinkage =

$$\frac{\text{original length} - \text{length after shrinkage}}{\text{original length}} \times 100,$$

for the length of the side edge of the portion in which the water-absorbing shrinkable fibers are provided. Furthermore, the shrinking force means the tensile force that must be applied to the water-absorbing shrinkable fibers, after they have been shrunk, in order to stretch them back to their original non-shrunk length, after they have been wetted with urine and shrunk. More specifically, a sample is attached to a Tensilon tester while adjusting the grip distance to 50 mm, the sample is wetted with artificial urine and the shrinking force (g) is measured.

Provided that the foregoing effects are attained by the water-absorbing shrinkable fibers, specific embodiments of the invention are not limited to those specifically disclosed in the drawings. For example, if the shrinking force of the water-absorbing shrinkable fibers is insufficient, composite fibers comprising a plurality of kinds of water-absorbing shrinkable fibers can be used, or water-absorbing shrinkable fibers can be used in combination with other fibers after they have been twisted together or woven or knitted together. Moreover, water-absorbing shrinkable fibers can be combined with other material by sewing a woven or knitted fabric or non-woven fabric with a yarn of the water-absorbing shrinkable fibers. Moreover, the water-absorbing shrinkable fibers 2 can be fixed not only adjacent to the water-absorbing layer, but also, along the edge in the lengthwise direction of the disposable diaper 1, or the water-absorbing shrinkable fibers may be fixed on the surface sheet 3. In each case, the intended effects can similarly be attained. However, if the water-absorbing shrinkable fibers 2 are placed on the water-absorbing layer 4, because the water-absorbing layer 4 is formed of a less flexible and elastic material, such as fluffed pulp or paper, even when the water-absorbing shrinkable fibers 2 shrink, the characteristics of the water-absorbing shrinkable fibers 2 are scarcely transmitted to the water-absorbing layer 4, with the result being that a liquid seal is not formed. The water-absorbing shrinkable fibers 2 need not be mounted in the illustrated linear form. For example, in the case of a disposable diaper having an hourglass-like shape, the water-absorbing shrinkable fibers 2 can be fixed along the hourglass-like shape according to the configuration of the crotch portion. Furthermore, the length of the water-absorbing shrinkable fibers 2 should not be such that the entire length in the lengthwise direction of the diaper is covered. When the fibers 2 have a high percentage shrinkage, the fibers 2 need not be very long. However, in order to attain the shrinking effect along the entire length of the crotch portion of the diaper uniformly, the water-absorbing shrinkable fibers 2 should be placed along the central portion in the lengthwise direction of the diaper, and in order to further enhance this effect, it is preferred that the central portion of the water-absorbing shrinkable fibers be substantially symmetrical with the central portion in the lengthwise direction of the disposable diaper.

As the water-absorbing shrinkable fibers 2 that can be used for the disposable diaper of the present invention, there can be mentioned, for example, modified cellulose fibers, such as those of cotton and rayon, for example, carboxymethylated cotton, methylated cotton and ethylated cotton fibers, as disclosed in our previous patent application entitled "TWISTED COMBINATION YARN", which was filed on June 19, 1980 (Japanese Patent Application No. 83390/80).

For further illustration of the disposable diaper of the present invention, Referential Examples and Examples will now be described.

REFERENTIAL EXAMPLE 1

A cotton yarn (twisted three yarns of a count number of 60, supplied by Daiwabo Kabushiki Kaisha) was carboxymethylated according to a conventional procedure. The percent shrinkage and shrinking force of the treated yarn when it was wetted with physiological saline solution are shown in Table 1. Incidentally, in the Table, DS designates the etherification degree.

REERENTIAL EXAMPLE 2

A polynosic rayon yarn (twisted three yarns of a count number of 30, supplied by Daiwabo Kabushiki Kaisha) was treated in the same manner as in Referential Example 1. 1 The percent shrinkage and shrinking force are shown in Table 2.

TABLE 1

| Sample No. | DS | Percent Shrinkage (%) | Shrinking Force (g) | Remarks |
|---|---|---|---|---|
| 1 | 0.21 | 10 | 9.7 | |
| 2 | 0.25 | 15 | 12.1 | |
| 3 | 0.27 | 25 | 16.4 | |
| 4 | 0.30 | 38 | 19.3 | |
| 5 | 0.34 | 48 | 21.8 | |
| 6 | 0.37 | 54 | 20.7 | |
| 7 | 0.44 | — | — | dissolved |

TABLE 2

| Sample No. | DS | Percent Shrinkage (%) | Shrinking Force (g) | Remarks |
|---|---|---|---|---|
| 8 | 0.18 | 13 | 22.8 | |
| 9 | 0.24 | 22 | 33.0 | |
| 10 | 0.29 | 35 | 38.2 | |
| 11 | 0.34 | 39 | 38.5 | |
| 12 | 0.37 | — | — | dissolved |

From these data, it is seen that it is preferred that the etherification degree of a carboxymethylated cotton yarn be 0.27 to 0.40 and the etherification degree of a carboxymethylated polynosic rayon yarn be 0.20 to 0.35.

REFERENTIAL EXAMPLE 3

When carboxymethylation was carried out in the same manner as in Referential Example 1, 3% (based on the cellulose) of epichlorohydrin was added as a cross-linking agent and cross-linking was simultaneously effected. The percent shrinkage and shrinking force of the thus-treated cotton yarn were measured. The results shown in Table 3 were obtained.

REFERENTIAL EXAMPLE 4

A polynosic rayon was treated in the same manner as in Referential Example 3, and the percent shrinkage and shrinking force were measured. The results shown in Table 3 were obtained.

From the data shown in Table 3, it is seen that when the cross-linking treatment is carried out, the etherification degree can be increased.

TABLE 3

| Sample No. | DS | Percent Shrinkage (%) | Shrinking Force (g) | Remarks |
|---|---|---|---|---|
| 13 | 0.44 | 56 | 16.5 | Referential Example 3 |
| 14 | 0.38 | 42 | 40.3 | Referential Example 4 |

In Tables 1 through 3, each of the values of the shrinking force is one as calculated on the yarn size of 13.3 counts.

EXAMPLE 1

A disposable diaper having a structure as shown in FIG. 3 was prepared by using the following materials.
Surface Sheet:
  Non-woven fabric having a basis weight of 20 g/m$^2$, which was formed by heat-bonding 45% of polyester fibers (1.5 d×64 F) and 55% of ES fibers (3 d×51 f)
Water-Absorbing Layer:
  36 g of fluffed pulp covered with moisture-proof water-absorbing paper
Water-Absorbing Paper:
  Moisture-proof, water-absorbing paper
Back Sheet:
  Polyethylene film having a basis weight of 25 g/m$^2$
Water-Absorbing Shrinkable Fibers:
  Yarn prepared in Referential Example 1 or 3 was twisted with cotton yarn (twisted three yarns of a count number of 60, supplied by Daiwabo Kabushiki Kaisha) and cut in a length of 200 mm, and 15 mix-twisted yarns were gathered into a bundle. Yarn prepared in Referential Example 2 or 4 was treated in the same manner except that a bundle was formed by gathering 5 mix-twisted yarns. These yarns were fixed at intervals of 20 mm by hot melting (runs Nos. 1 through 10 and 13 and 14).

EXAMPLE 2

A disposable diaper was prepared in the same manner as described in Example 1, except that in order to examine the influences of the yarn size, a bundle of 20 yarns prepared in Referential Example 1 or a bundle of 7 yarns prepared in Referential Example 2 was used as the composite assembly of the water-absorbing shrinkable fibers (runs Nos. 11 and 12).

The percent shrinkages and shrinking forces of the thus-prepared disposable diapers are shown in Table 4.

EXAMPLE 3

A disposable diaper was prepared in the same manner as in Example 1, except that the water-absorbing shrinkable fibers were sewn to water-absorbing waterproof paper at intervals of 10 mm. The shrinkage percent and shrinking force of the thus-prepared diaper are shown in Table 5.

TABLE 4

| Run No. | Sample No. | Percent Shrinkage (%) | Shrinking Force (g) | Remarks |
| --- | --- | --- | --- | --- |
| 1 | 1 | 5 | 41 | comparison |
| 2 | 2 | 8 | 65 | comparison |
| 3 | 3 | 17 | 102 | present invention |
| 4 | 4 | 24 | 116 | present invention |
| 5 | 5 | 30 | 121 | present invention |
| 6 | 6 | 28 | 115 | present invention |
| 7 | 11 | 27 | 132 | present invention |
| 8 | 10 | 26 | 125 | present invention |
| 9 | 9 | 18 | 115 | present invention |
| 10 | 8 | 9 | 73 | comparison |
| 11 | 4 | 27 | 114 | present invention |
| 12 | 10 | 28 | 118 | present invention |
| 13 | 13 | 33 | 126 | present invention |
| 14 | 14 | 31 | 135 | present invention |

TABLE 5

| Run No. | Sample No. | Percent Shrinkage (%) | Shrinking Force (g) | Remarks |
| --- | --- | --- | --- | --- |
| 15 | 4 | 23 | 123 | present invention |
| 16 | 10 | 24 | 130 | present invention |

It is understood from the above mentioned examples and comparative examples that the diaper of the invention has advantages such that it fits well to the body, especially while wetted, and does not get stuffy so much. In the diaper using bundles of water-absorbing shrinkable yarns, the percent shrinkage of the yarn tends to be reduced because of friction between yarns and then between the yarn and the top sheet or back sheet, and the action of the fixing member. Nevertheless the shrinking force of the yarn tends to be increased. This is the reason for the above mentioned advantages. Accordingly the diaper may be successfully made of yarns of relatively low a shrinking force.

The embodiments of the invention in which an exclusive property or privilege is claimed are defined as follows:

1. A disposable diaper comprising a liquid-permeable surface sheet, a liquid-impermeable back sheet, a water-absorbing layer located between said sheets, and water-absorbing shrinkable fibers which shrink in the direction of the fiber length and are rendered elastic on absorption of water, said water-absorbing shrinkable fibers being fixed along the central portion and extending in the lengthwise direction of the disposable diaper and being located so that said water-absorbing shrinkable fibers are not placed on the water-absorbing layer but are capable of being wetted when the diaper is wetted, said water-absorbing shrinkable fibers, when wetted, exhibiting a percent shrinkable of at least 15% and a shrinking force of at least 100 g.

2. A disposable diaper as set forth in claim 1, wherein said water-absorbing shrinkable fibers are composite fibers formed of a plurality of kinds of fibers.

3. A disposable diaper as set forth in claim 1 or claim 2, wherein said water-absorbing shrinkable fibers are fixed along the edges in the lengthwise direction of the disposable diaper.

4. A disposable diaper as set forth in claim 1 or claim 2, wherein said water-absorbing shrinkable fibers are fixed between said surface sheet and said back sheet.

5. A disposable diaper as set forth in claim 1, including an absorbent paper extending from said water-absorbing layer to said water-absorbing shrinkable fibers for transferring liquid from said water-absorbing layer to said fibers.

6. A disposable diaper as set forth in claim 1, wherein said water-absorbing shrinkable fibers are formed of carboxymethylated cellulose.

7. A disposable diaper as set forth in claim 6, wherein said water-absorbing shrinkable fibers are formed of crosslinked carboxymethylated cellulose.

8. A disposable diaper as set forth in claim 6, wherein said water-absorbing shrinkable fibers are carboxymethylated cotton yarns in which the etherification degree is 0.27 to 0.40.

9. A disposable diaper as set forth in claim 6, wherein said water-absorbing shrinkable fibers are carboxymethylated polynosic rayon yarns in which the etherification degree is 0.30 to 0.40.

10. In a disposable diaper comprising a liquid-absorbing layer located between a liquid-permeable surface sheet and a liquid-impermeable backing sheet, the side edges of said liquid-absorbing layer being laterally inwardly spaced from the side edges of said sheets, said diaper having a central portion adapted to be extended between the legs of the wearer and having front and rear portions adapted to be secured together around the waist of the wearer and wherein the liquid-permeable surface sheet is adapted to be disposed facing the body of the wearer and the liquid-impermeable backing sheet is adapted to be disposed facing away from the body of the wearer, the improvement which comprises: a pair of strips disposed close to the respective side edges of said sheets in the central portion of said diaper and extend lengthwise therealong, said strips being located between said sheets and being laterally outwardly spaced from the respective side edges of said liquid-absorbing layer; said strip being comprised of liquid-absorbing, lengthwise-shrinkable fibers which shrink and become elastic when they are wetted with liquid so that when said fibers absorb liquid and shrink, the side edges of said central portion of diaper are drawn into snug engagement with legs of the wearer to minimize liquid leakage, said fibers, when wet, having a percent shrinkage of at least 15% and exhibiting a shrinkage tensile force of at least 100 g.

* * * * *

UNITED STATES PATENT AND TRADEMARK OFFICE
CERTIFICATE OF CORRECTION

PATENT NO. : 4,357,938
DATED : November 9, 1982
INVENTOR(S) : Osamu Ito et al

It is certified that error appears in the above-identified patent and that said Letters Patent is hereby corrected as shown below:

Column 7, line 56; change "shrinkable" to --shrinkage--.
Column 8, line 48; change "strip" to --strips--.

Signed and Sealed this

Eighth Day of March 1983

[SEAL]

Attest:

GERALD J. MOSSINGHOFF

Attesting Officer   Commissioner of Patents and Trademarks